United States Patent
Valenti et al.

(10) Patent No.: US 11,259,790 B2
(45) Date of Patent: Mar. 1, 2022

(54) INTERFACE DEVICE BETWEEN SURGICAL INSTRUMENTS OR LAPAROSCOPES AND ORGANS OR VISCERA

(71) Applicants: Gabriele Valenti, Rome (IT); Valentina Valenti, Rome (IT); Sebastiano Sciarretta, Rome (IT)

(72) Inventors: Gabriele Valenti, Rome (IT); Valentina Valenti, Rome (IT); Sebastiano Sciarretta, Rome (IT)

(73) Assignees: Gabriele Valenti, Rome (IT); Valentina Valenti, Rome (IT); Sebastiano Sciarretta, Rome (IT)

( * ) Notice: Subject to any disclaimer, the term of this patent is extended or adjusted under 35 U.S.C. 154(b) by 468 days.

(21) Appl. No.: 16/463,290

(22) PCT Filed: Nov. 23, 2017

(86) PCT No.: PCT/IT2017/000266
§ 371 (c)(1),
(2) Date: May 22, 2019

(87) PCT Pub. No.: WO2018/100593
PCT Pub. Date: Jun. 7, 2018

(65) Prior Publication Data
US 2019/0307440 A1    Oct. 10, 2019

(30) Foreign Application Priority Data
Nov. 29, 2016 (IT) .................. 102016000120800

(51) Int. Cl.
A61B 1/32      (2006.01)
A61B 17/02     (2006.01)
A61B 17/00     (2006.01)

(52) U.S. Cl.
CPC .. *A61B 17/0218* (2013.01); *A61B 2017/0042* (2013.01); *A61B 2017/00225* (2013.01); *A61B 2017/00477* (2013.01); *A61B 2017/00557* (2013.01); *A61B 2017/00862* (2013.01);
(Continued)

(58) Field of Classification Search
CPC combination set(s) only.
See application file for complete search history.

(56) References Cited

U.S. PATENT DOCUMENTS

| | | |
|---|---|---|
| 4,592,355 A | 6/1986 | Antebi |
| 5,359,995 A | 11/1994 | Sewell, Jr. |
| 5,400,773 A | 3/1995 | Zhu et al. |

(Continued)

FOREIGN PATENT DOCUMENTS

| | | |
|---|---|---|
| EP | 0117981 | 9/1984 |
| EP | 0610099 | 8/1994 |

(Continued)

*Primary Examiner* — Sameh R Boles
(74) *Attorney, Agent, or Firm* — Pearne & Gordon LLP

(57) ABSTRACT

Described is a surgical device to retain and move an organ during surgical operations, which makes it possible to easily prepare the system for holding the organ and avoids the need both for a dedicated access trocar for exclusive use and the insertion of an operating member connected irreversibly to the surgical device. The surgical device minimises the risk of tearing and/or bleeding of the organ following the actions applied on the same organ during the surgical operation.

15 Claims, 3 Drawing Sheets

(52) U.S. Cl.
CPC ............... *A61B 2017/00876* (2013.01); *A61B 2017/0225* (2013.01)

(56) References Cited

U.S. PATENT DOCUMENTS

| | | | |
|---|---|---|---|
| 5,425,705 | A | 6/1995 | Evard et al. |
| 5,439,476 | A | 8/1995 | Frantzides |
| 5,450,842 | A | 9/1995 | Tovey et al. |
| 5,588,951 | A | 12/1996 | Zhu et al. |
| 5,613,973 | A | 3/1997 | Hart et al. |
| 5,782,839 | A * | 7/1998 | Hart .................. A61B 17/0218 606/110 |
| 5,855,586 | A | 1/1999 | Habara et al. |
| 6,015,382 | A | 1/2000 | Zwart et al. |
| 6,371,910 | B1 | 4/2002 | Zwart et al. |
| 9,737,694 | B1 | 8/2017 | Shah et al. |
| 10,028,734 | B2 | 7/2018 | Lessing et al. |
| 10,172,602 | B2 | 1/2019 | Lessing et al. |
| 2002/0091301 | A1 | 7/2002 | Levin |
| 2005/0187566 | A1 | 8/2005 | Byrum |
| 2009/0082724 | A1 | 3/2009 | Shah et al. |
| 2015/0182229 | A1 | 7/2015 | Shah et al. |
| 2015/0190142 | A1 | 7/2015 | Shah et al. |
| 2016/0135799 | A1 | 5/2016 | Lessing et al. |
| 2018/0325507 | A1 | 11/2018 | Lessing et al. |

FOREIGN PATENT DOCUMENTS

| | | |
|---|---|---|
| EP | 0611561 | 8/1994 |
| FR | 2980355 | 3/2013 |
| WO | 9416630 | 8/1994 |
| WO | 9920321 | 4/1999 |
| WO | 2015157621 | 10/2015 |
| WO | 2016077358 | 5/2016 |

* cited by examiner

TABLE I

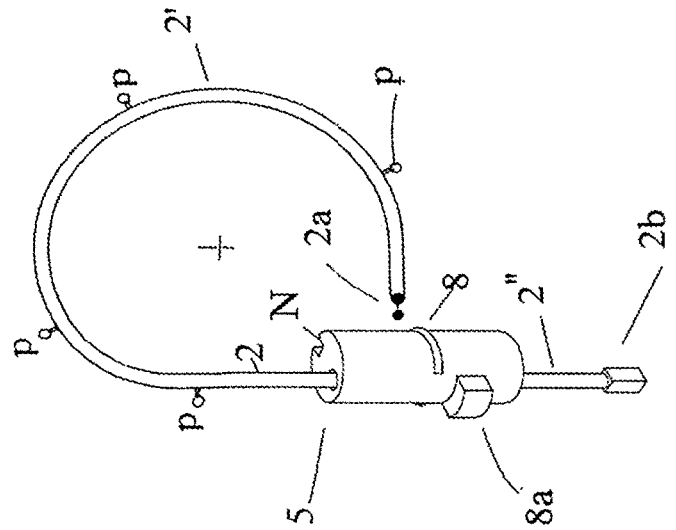
TABLE II
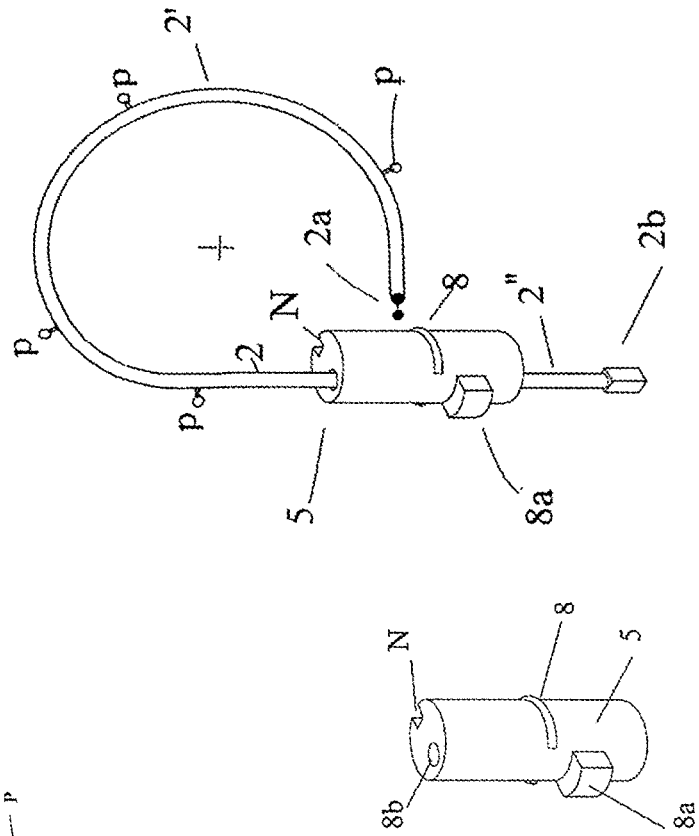
Fig. 4
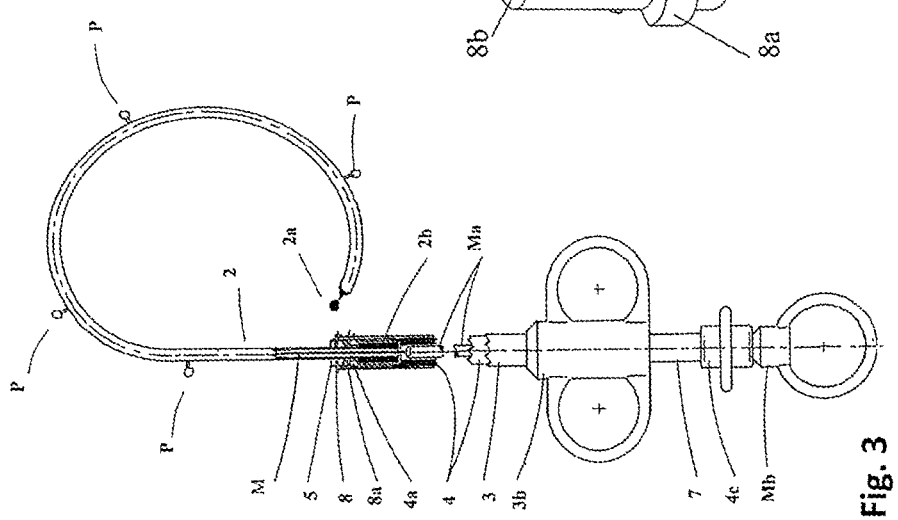
Fig. 3
Fig. 5

TABLE III

INTERFACE DEVICE BETWEEN SURGICAL INSTRUMENTS OR LAPAROSCOPES AND ORGANS OR VISCERA

This invention relates to a surgical device to retain and move an organ or viscera during surgical operations, which makes it possible to easily prepare the system for holding the organ or viscera and avoids the need both for a dedicated access trocar for exclusive use and the passage of an operating member connected irreversibly to the surgical device. The surgical device minimises the risk of tearing and/or bleeding of the organ or viscera following the actions applied on the same organ or viscera during the surgical operation.

During surgical operations, especially laparoscopic operations, the exposure of the operating area is achieved through traction, suspension devices, thrusts exerted by rigid and traumatising gripping instruments on delicate and fragile tissues which often tear, bleed, escape from grip. Instruments have been made with various configurations, which, when inserted in abdomens through an access trocar and a dedicated movement handle, use the identical principle of increasing their surface area mechanically or pneumatically, and operate as blades or "small hands" to move the viscera.

The aim of this invention is to provide a surgical device to anchor with an organ or viscera by which it is possible to retain and to move an organ or viscera with the usual instruments used currently in operating rooms without an access trocar and a handpiece being dedicated exclusively to the use of the surgical device, without the organ or viscera escaping from grip.

These aims are achieved by a device for surgical operations comprising an elongate body configured to be applied and guided for retaining at least one organ or viscera of a patient and a retaining element integral with the body.

By means of a trocar of the type usually used in laparoscopy access is gained to the abdomen through a duct, which has the purpose of guiding the body with the retaining element, and an operating member designed to be slidably housed in the duct and which will both be completely removed once the surgical device is positioned.

The operating member being configured to cause an escape of the body from the duct and a withdrawal of the body into the duct.

A possible embodiment of the invention may have at least one of the following technical aspects.

Preferably, the device comprises the retaining element fitted on the body and configured for being slidably positioned in the duct during the escape of the body from the duct.

Preferably, the retaining element is configured to remain integral with the movement of the body during the escape of the body from the duct.

Preferably, the retaining element is configured to grip an anchoring section of the duct, in such a way as to allow the sliding of the body with respect to the retaining element during the withdrawal of the body into the duct.

Preferably, the anchoring section corresponds to the distal end section of the duct.

Preferably, the retaining element is designed to receive the body in such a way that the body remains inserted through the retaining element during the escape and the withdrawal.

Preferably, the retaining element is designed to prevent the sliding of the body with respect to the retaining element during the escape of the body from the duct.

Preferably, the device comprises constraining means between the retaining element and the body configured so that the retaining element is designed to follow the body and/or to remain integral with the body during the escape.

The constraining means are therefore designed to prevent the sliding of the body relative to the retaining element during the escape.

Preferably, the constraining means between the retaining element and the body, when the retaining element is gripped to the duct, are configured to allow the sliding of the body with respect to the retaining element during the withdrawal of the body into the duct.

Preferably, the constraining means between the body and the retaining element are designed in such a way that the body cannot move with respect to the retaining element, except when the retaining element is gripped to the duct. Therefore, when the retaining element passes beyond the anchoring section which corresponds to the distal end section of the duct, the body surrounds the organ in a predetermined position which cannot be modified and its further increase or reduction in circumference is not possible.

Preferably, the constraining means form part of the retaining element.

The retaining element may be, for example, a self-locking ring suitable to be jammed associated with a non-return spring.

Another possibility without limiting the scope of the invention is that the retaining element is shaped in such a way as to have constraining means easily de-activated by the surgeon, to pass from a step of preventing the sliding to another moment of free sliding of the body in the retaining element also in a step wherein the retaining element is no longer clinging to the duct. By way of an example and without limiting the scope of the invention, in the retaining element there is the constraining element in the faun of a choker button system which locks the body and when pressed allows the free sliding of the body through the retaining element.

This makes it possible to modify the diameter of the surgical device by widening it or narrowing it. Therefore, when required, it is possible to modify the seat of its application.

Preferably, the duct is designed to guide the escape and the withdrawal of the body along a direction parallel to an axis of extension of the body and to an axis of extension of the duct.

Preferably, the device comprises a shape memory type element, a so-called "spring", configured in such a way that at least a distal portion of the body is designed to progressively adopt, during the escape, a shape at least partly annular, designed to surround at least partly the organ or viscera.

Preferably, the spring is made integral at least partly with the operating member and slides inside the body, or is part of the body.

Preferably, the spring is designed to stiffen and to adopt elastically and progressively the annular shape of the body, during the escape from the duct, with the aim of facilitating the surrounding of the organ or viscera.

Preferably, the spring has the purpose of facilitating the approach of the coupling and attachment means. The approach is obtained by moving the distal portion of the body close to the retaining element or close to the body.

Preferably, the spring is removed once the coupling or attachment closure movement of the body on itself or on the retaining element is completed.

Preferably, therefore, the device comprises coupling or attachment means.

Preferably, the attachment or coupling means are integral with the distal end of the body and configured so that the at least one distal portion connects to the retaining element or couples on itself and maintains the at least partly annular shape.

These attachment or coupling means may be of a mechanical and/or magnetic and/or thermal type, or even of the Velcro type or the like.

Preferably, once the attachment or coupling means are joined to the retaining element or to the body the spring completes its function and is removed definitively and the body loses the relative rigidity and returns to its operational elasticity and softness.

The at least partly annular shape may maintained in any case by means of any other simple closure, to facilitate, for example, the laparoscopic positioning, in a secure manner, and, therefore, such as not to open with traction operations.

Moreover, once the coupling or the connection has been made, the length of the distal portion of the body, that is to say, the one extended from the retaining element to the coupling or attachment means, can preferably be adjusted as a function of the volume of the organ to be surrounded.

The invention of Tovey H. Jonathan et Al. No. U.S. Pat. No. 5,450,842 A of 19 Sep. 1995 describes a retractor for moving organs, the aim of which is to overcome the limits of the diameter of access trocars and the limitations and the trauma of straight retractors in which the distal end may be very traumatising. The device forces the use of a dedicated access trocar, which is always manoeuvred from the outside by a handpiece; it may be retracted and advanced several times and uses the properties of a thermoplastic material, which once in the abdomen bends partly on itself, transforming a straight instrument with the more distal part in the form of a tip into an almost circular instrument, therefore having a flat surface, an operating surface variously configurable, but wherein the most distal part is represented by a curve, so, therefore, not very traumatising. The purpose which it aims to achieve is to distribute and improve the contact surface with the tissues, eliminating the distal end which bends on itself and reducing the risk of trauma to the organs and viscera.

Preferably, the surgical device according to this invention has the long distal portion of the body between the retaining element and the distal end of the body, in various points of its circumference of the gripping means by which the distal portion, once applied for retaining the organ, can be moved and/or retained for moving and/or retaining the organ or viscera.

Preferably, the gripping means are shaped in such a way as to be grasped securely and easily with the laparoscopic instruments already in use in operating rooms and prevent the possible direct contact between laparoscopic gripping instruments and organs and prevent the risk of direct gripping on the body; in effect, in the absence of gripping means, the laparoscopic grippers would grip exclusively the body of the surgical device clamped around the organ, with the exposure to the risk of accidental and involuntary pinching of the organ.

The invention of Hart Collin P. Et AL No. U.S. Pat. No. 5,782,839 A proposes a surgical device for picking up and handling organs which also comprises a handpiece which acts as an operating member irreversibly connected to a belt which surrounds the organ. The instrument forces the introduction of a dedicated trocar for exclusive use for access to the abdominal cavity. It has been exposed to the risk of losing gas and fluids.

The operating cannula has a fixed orientation, linked to the site for access to the abdominal cavity; moreover, the belt which surrounds the organ has a single and unmodifiable point of joining with the cannula with the drawback that the organ surrounded may swing by gravity. The sum of these 2 constraints limits the freedom of handling the organs so as to expose the operating field and in order to work on desired planes. In order to limit these drawbacks, the belt proposed must be semi-rigid, therefore relatively traumatic.

On the other hand, returning to the subject of this invention, preferably the body, which is atraumatic and elastic, detaches from the operating member which is removed with the retaining element, once application around the organ is completed. The body can be gripped by means of its gripping means by any laparoscopic instrument or gripper and introduced through any trocar for access to the abdominal cavity. The body may be momentarily released and then re-gripped depending on the operating time, and can be gripped at various points of the circumference: this is the interface between the organs and the surgical instruments. 2 or more surgical devices can also be applied on the same organ and the same gripper can exert the grip on one of the surgical devices according to requirements.

Preferably, the device comprises pushing element in such a way as to cause the escape from the duct of the body with the retaining element and the spring, the pushing element being integral with the operating member.

The pushing means are preferably inside the operating member, and are coupled to the operating member so that the spring follows the escape of the elongate body from the duct.

The user must therefore eject the body from the duct, applying a pushing action forwards on the operating member, so that the body escapes from the duct and adopts, thanks to the spring, a shape at least partly annular designed to surround an organ or viscera. Once the body has adopted this embodiment, the surgeon couples the distal end of the body on itself to the distal portion, or to the retaining element, in such a way that the distal portion maintains the closed and irreversible circumferential shape.

If the distal portion couples on itself, this at least partly annular embodiment is basically a shape which closes on itself. From this moment the spring, which until now has been integral with the body, may be definitively removed and the body returns to its softness and elasticity.

Preferably, the retaining element is configured to grip onto the duct in such a way that the withdrawal of the body in the duct allows the adjustment of the extension of the distal portion once it has adopted the at least partly annular shape.

Once the body has escaped sufficiently, in such a way that the distal portion has adopted the shape, and once the distal portion has been coupled or attached on itself or on the retaining element in such a way that it substantially maintains the circumferential shape, the surgeon pulls the movement member in a direction opposite to the previous pushing action, in such a way as to withdraw the proximal portion of the body in the duct, and adjust the extension of the distal portion, and/or its inner tension.

In this way, the system of forces which the distal portion of the body applies on the organ or viscera is adjusted.

Preferably, the operating member is designed to release the body after the escape of the operating member from the distal end section of the duct, in an automatic fashion.

Preferably, the operating member can slide in the duct along the axis of extension of the duct.

Preferably, the device comprises means for coupling between the operating member and the body, in such a way that the operating member can cause an escape of the body from the duct and a withdrawal of the body into the duct.

Preferably, the coupling means are configured so that the operating member can release the body, preferably automatically, following the escape of the operating member from the duct.

Preferably, using the coupling means the operating member is designed to grasp a proximal end of the body in a releasable manner, so as to cause the escape and the withdrawal of the body.

The coupling means comprise, by way of example, two gripping arms belonging to the operating member which tend to mutually move away in an elastic fashion, in such a way that the operating member is designed to release the body after the escape of the operating member from the duct.

Preferably, the device comprises a block designed to limit the travel of the operating member inside the duct and/or along the duct, in such a way as to prevent the escape of the operating member from the duct and to prevent the retaining element from freeing from the end of the duct at an undesired time.

Preferably, the block is removable.

Preferably, the block can be associated removably with the operating member.

The block is used, preferably, so that the operating member can also withdraw the body into the duct, once the distal portion has adopted the at least partly annular form and its has been coupled on itself and/or on the retaining element. In this way, by means of the same operating member, the user is able, in an initial moment, to make the distal portion adopt the at least partly annular form, and in a subsequent moment is also able to adjust the extension of the distal portion and/or its inner tension, withdrawing the body into the duct.

The retaining element preferably comprises at least one anchoring spring.

Preferably, the anchoring spring is configured to adopt an operational sliding condition, wherein it is designed to slide in the duct and/or along the duct during the escape of the elongate body from the duct.

Preferably, when the anchoring spring adopts this sliding condition, the retaining element is designed to follow and/or to remain integral with the elongate body during the escape of the elongate body from the duct.

Preferably, the anchoring spring is configured to adopt an operational anchoring condition wherein it is designed to remain anchored and/or blocked to the anchoring section of the duct, and/or to oppose the anchoring section.

Therefore, when the anchoring spring adopts this operational anchoring condition, the anchoring spring is designed so that the retaining element grips and/or remains gripped to the duct, in such a way that, in the direction of withdrawal of the body into the duct, the movement of the retaining element with respect to the duct is prevented.

Preferably, when the anchoring spring adopts the anchoring condition, the constraining means between the retaining element and the body are designed to ensure that the body can slide relative to the retaining element, during the withdrawal of the body in the duct.

Preferably, the anchoring spring is configured to pass automatically from the sliding condition to the anchoring condition, when the retaining element passes through the anchoring section in the direction of escape of the body from the duct. Once the retaining element passes through and exceeds the anchoring section the escape and definitive separation of the body from the duct is obtained.

In one particular embodiment of the invention, the elongate body, with which the organ is surrounded, consists of an inflatable structure, like a slim doughnut, an air chamber, which, once inflated under pressure, reaches the volume and the predetermined shape. A further increase in the blowing pressure does not alter the shape and volume, but only the consistency of the surgical device as occurs for the prior art angioplasty catheters or oesophageal or intestinal expansion.

Preferably, a one-way valve is integral with the inflatable structure.

Preferably, the inflation means comprise a pipe in fluid-dynamic communication, on a first end, with the valve of the inflatable structure and, on a second end opposite the first end, with the pumping means. The valve being on the inflatable structure.

Preferably, the pipe is advantageously removable from inflatable structure.

Preferably, the surgical device when it is deflated has a ribbon-like aspect, like a long tubular element without tone, which is introduced easily into the abdomen through a trocar and with which the organ is surrounded.

Preferably, the surgical device inflated under pressure returns to the ring shape and the predetermined volume, with a hard, but elastic, consistency.

Preferably, the inflatable structure is configured so that the two ends of the body, proximal and distal, are automatically in close contact and the organ remains gripped in an atraumatic manner inside the ring.

Preferably, the device comprises coupling or attachment means at its two ends, which can be used before or after the inflation. Preferably, the inflatable body comprises gripping means along its circumference.

Preferably, the gripping means are shaped in such a way that they can be gripped securely and easily with the laparoscopic instruments already in use in operating rooms and prevent possible direct contact between laparoscopic gripping instruments and organs and prevent the risk of direct gripping on the body.

The inflatable surgical device is in way related to the invention of UNOV LOMA LINDA MED No. WO 94/16630 A1, or that of AHLUWALIA PRABHAT K No. U.S. Pat. No. 5,425,705 or the other of TRIGONON INC No. EP 0 610 099 A2 or that of U.S. Pat. No. 5,359,995 A, in which the identical principle is always used of increasing the surface of the surgical device which is in contact with the tissues of the patient. This increase in volume of the surgical device is obtained pneumatically or mechanically and allows the organs or viscera to be pushed or moved with instruments which are not very traumatising for their surfaces. A cannula, introduced in the abdomen through a dedicated access trocar for exclusive use, acts as an operating member and remains irreversibly anchored to the surgical device both for increasing and reducing the volume (for extracting at the end of the procedure) and for transmitting to the organs the pressures, tractions, pushing forces and movements exerted on the surgical device.

According to this invention, the surgical device has a predetermined shape and volume for surrounding an organ and only when inflated under pressure does it adopt its circumferential morphology, in the form of a doughnut, wherein the two ends come into contact and prevent the escape of the organ. The gripping means positioned on the outer surface of the surgical device are the points on which the laparoscopic grippers grip only when required without inserting in the abdomen further trocars or dedicated operating members.

The features of this invention are described in detail below by way of a non-limiting example of the more general technical concepts claimed.

The detailed description which follows relates to the accompanying drawings where in Table I we find FIGS. 1 and 2 in which:

FIGS. 1b and 1c show an example wherein the coupling means positioned at the distal end of the body attach on the distal portion of the body.

FIGS. 2a, 2b, 2c comprise an additional component of the first embodiment and refer respectively to the same instants of the method according to the respective FIGS. 1a, 1b, and 1c;

FIG. 2d shows a part of the components shown in FIGS. 2a-2c, in a successive moment of the same method;

In Table II.

FIG. 3 shows the surgical device with its fundamental elements in an example of the coupling or attachment means positioned between the distal end of the body and the retaining means.

FIG. 4 shows the detail of the single retaining element with the pushbutton constraining means which can be managed by the surgeon, with the anchoring ring, and a slot with guide for receiving the coupling means positioned on the distal end of the body.

FIG. 5 shows the surgical device with its two components, body and retaining element, the hooks which remain connected to the viscera or to the organ to perform its interface function with the surgical laparoscopic instruments. For demonstration purposes, the retaining element previously schematically illustrated in FIG. 4 is connected to the body which it passes through, and the distal ends of which are still not attached to the retaining means as should be the case for detaching from operating member.

In Table III

Figure 7:
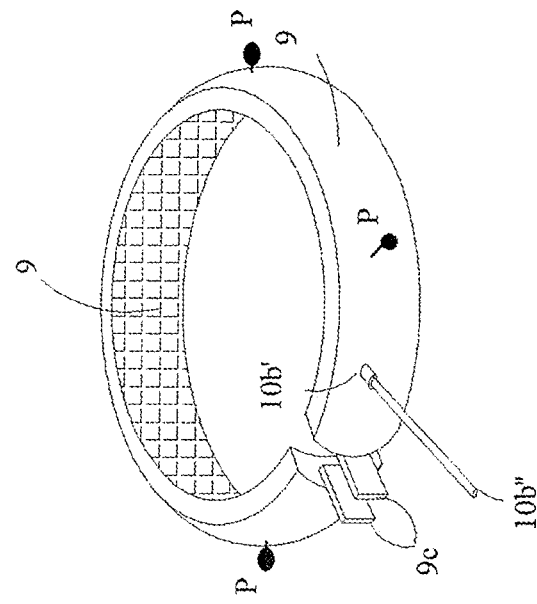
Figure 6:
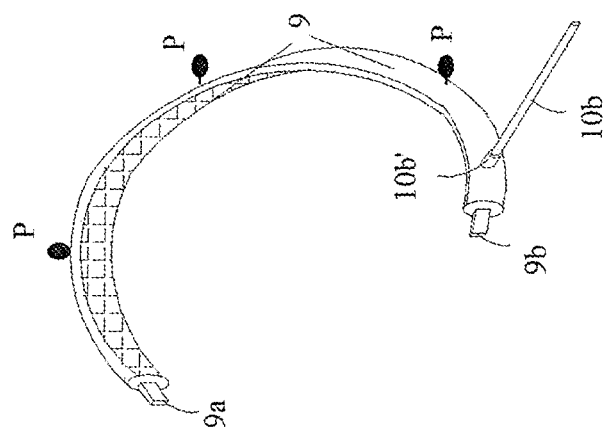

FIGS. 6 and 7 show the second embodiment of the invention, the inflatable structure, respectively in the step of introducing into the abdomen when deflated and in the step of inflation in which it is surrounded and it has captured the organ.

The accompanying drawings are not mutually to scale, in order to allow the most important technical aspects to be highlighted each time.

Numeral 1 in the drawings denotes a device according to a possible first embodiment of this invention.

The device 1 comprises an elongated body 2 configured to be used for retaining at least one internal organ of a patient.

The device comprises a duct 3 designed to guide the body 2 and an operating member 4 slidably housed in the duct 3.

In the first embodiment illustrated, the operating member 4 is designed to grip and/or grasp the body 2, to cause an escape of the body 2 from the duct 3, and/or a withdrawal of the body 2 in the duct 3.

The term "escape" of the body 2 from the duct 3 is used to mean a movement of the body 2 during which at least a part of the body 2 escapes the duct 3.

The term "withdrawal of the body 2 in the duct 3 is used to mean a movement of the body 2 during which at least part of the body 2 enters the duct 3.

The device comprises means for coupling between the operating member 4 and the body 2, by which the operating member 4 is configured for causing an escape of the body 2 from the duct 3, and/or a withdrawal of the body 2 in the duct 3. Thanks to these coupling means, the operating member 4 is also advantageously designed to grasp the body 2 or grip the body 2 in a releasable manner, as can be seen by comparing FIG. 2d with the other drawings.

The operating member 4 is also advantageously designed to grip or grasp the body 2 in an elastically releasable manner.

The operating member 4 is designed preferably to grip the body 2 and/or grasp the body 2 on a proximal end 2b of the body 2.

In the first embodiment illustrated, these coupling means between the operating member 4 and the body 2 comprise at least two gripping arms 4a and 4b belonging of the operating member 4 and able to grip the body 2, preferably on the proximal end 2b of the body 2.

In the first embodiment illustrated, these coupling means comprise a wide portion, integral with the body 2 and located preferably at the proximal end 2b of the body 2.

The wide portion is designed to remain gripped between the gripping arms 4a and 4b.

Advantageously, as will become clearer as this description continues, the arms 4a and 4b elastically tend to move mutually away to release the body 2, as shown in FIG. 2d.

The coupling means, in a possible embodiment not illustrated, might alternatively comprise a wire-like element integral with the body 2 and designed to be gripped by the operating member 4.

In order to cause the escape of the body 2 from the duct 3, and/or the withdrawal of the body 2 in the duct 3, the operating member 4 is designed to translate the elongate body 2 preferably along an axis of extension of the duct 3. The duct 3 is therefore designed to guide the elongate body 2 along the axis of extension of the duct 3.

In the first embodiment illustrated, the operating member 4 is designed to translate the elongate body 2 simultaneously also along the axis of extension of the elongate body 2. Therefore, during the translation of the elongate body 2 along the duct 3, the axis of extension of the elongate body 2 remains at least partly parallel to the axis of extension of the duct 3.

The operating situation of FIG. 1a coincides with that of FIG. 2a and the operating situations described in FIGS. 1b and 2b and in FIGS. 1c and 2c coincide, respectively.

The elongate body 2 is only partly shown in FIGS. 1a, 2a, 2b, 2c and 2d. The user, in a preparatory step for the use of the body 2 for retaining the organ or moving it, and starting, therefore, from the situation of FIG. 1a or 2a, applies a pushing action on the operating member 4, as indicated by the arrow X of FIGS. 1a and 2a. In this way, the operating member 4 determines the escape of the elongate body 2 from the duct 3, as can be seen by mutually comparing FIGS. 1a and 1b or 2a and 2b.

The escape of the body 2 from the duct 3 preferably occurs from a section of the distal end 3a of the duct 3. The withdrawal of the body 2 in the duct 3 also preferably occurs through the distal section 3a.

The distal section 3a of the duct 3 is that located furthest away relative to the zone where the user applies the force on the operating member 4.

With reference to FIGS. 1b and 1c, at least one distal portion 2' of the body 2 is designed for progressively adopting, during the escape of the body 2 from the duct 3, a shape designed to surround at least partly the organ. This embodiment defines at least part of a ring, and it is therefore at least partly annular. In the embodiment to which the drawings refer, the shape is preferably closed.

Preferably, the distal portion 2' comprises gripping means P by means of which the distal portion 2', once applied to retain the organ, can be moved and/or retained for moving and/or retaining the organ by the laparoscopic instruments and grippers normally used in operating rooms and not dedicated only to the function. The gripping means P, for reasons of clarity of the drawings and with reference to the first embodiment shown, are only partly illustrated and indicated, and only in FIG. 1c.

This closed shape of the distal portion 2' of the body 2 is only visible in FIGS. 1b and 1c. It should be noted that in FIGS. 1b and 1c, in order to show more clearly the components of the device 1, the at least one distal portion 2' is shown in a reduced scale and not proportional relative to the other components of the device 1, at least with regard to the first embodiment to which reference in this detailed description.

The device 1 comprises coupling or attachment means by which the distal portion 2' can couple on itself or to the retaining element 5 to maintain the at least partly annular shape, which in the embodiment illustrated is a closed shape.

These attachment or coupling means can be mechanical, magnetic, thermal or of another type. For example, the attachment or coupling means might be of the Velcro type. In the embodiment illustrated in FIGS. 1b and 1 c, the attachment or coupling means advantageously comprise a hook 2a integral with the distal portion 2'. The hook 2a is located advantageously at a distal end of the distal portion 2'. In the first embodiment illustrated, the hook 2a is configured so that the at least one distal portion 2' can fasten on itself and can keep the closed shape. FIGS. 3 and 5 show a solution wherein the distal portion 2' has attachment or coupling mans 2a which link directly to the retaining means.

The at least one distal portion 2' of the body 2 and the distal end 2a of the body 2 are situated along the elongate body 2, preferably on the opposite side of the proximal end 2b.

In order for the distal portion 2' to adopt the closed shape, during the escape of the body 2 from the duct 3, the at least one distal portion 2' comprises a spring tending to elastically adopt the closed shape.

Figure 2:
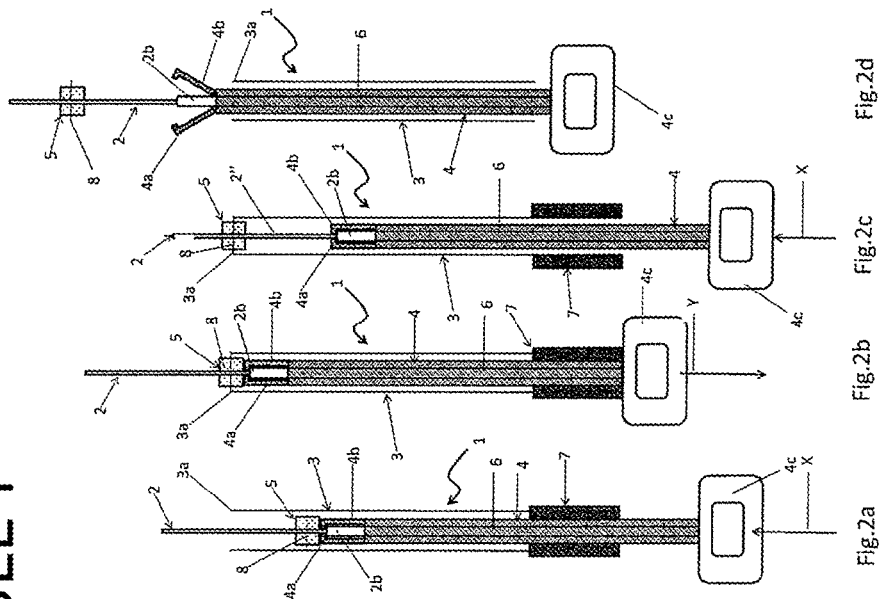
Figure 1:
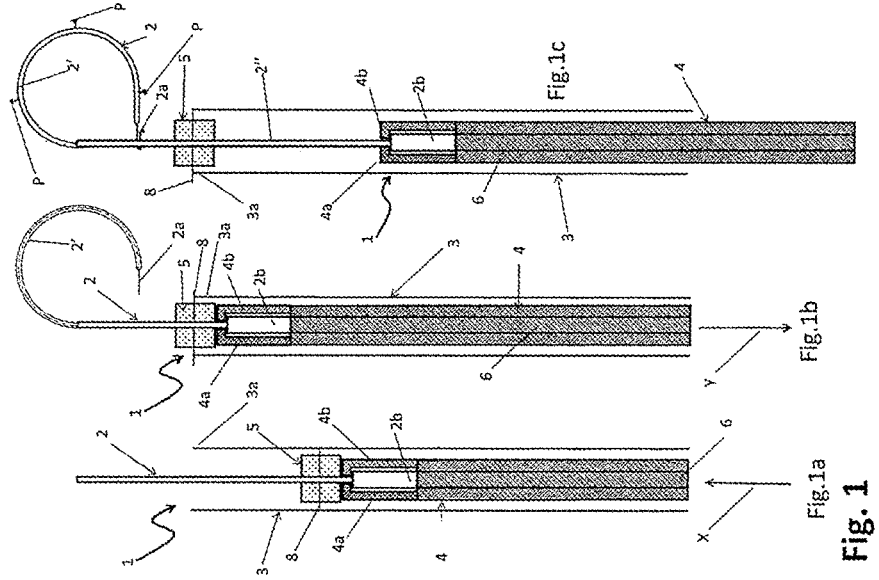
FIGS. 1a, 1b, 1c show a cross section of a part of a device according to a first possible embodiment of this invention during respective instants of a possible method for operation of the embodiment.

The spring, which is not illustrated in FIGS. 1 and 2, extends preferably along the axis of extension of the elongate body 2. The spring is preferably extended from the distal end of the distal portion 2', therefore in the vicinity of the attachment means or hook 2a, and proximal to the operating member.

The spring therefore acts as a guide with predetermined curvature for the elongate body 2, during the escape of the body 2 from the duct 3.

The device 1 advantageously comprises a pushing element 6 designed to push the spring in such a way as to cause the escape from the duct 3 together with the body 2. The pushing element 6 is preferably integral with the operating member 4, and is therefore preferably coupled to the same operating member 4 in such a way as to follow the movement.

The pushing means 6, in the embodiment illustrated, are designed to push the spring from the proximal end 2b of the body 2.

The pushing means 6, in the first embodiment illustrated, is designed to remove the spring from the distal section 3a of the duct 3.

The device 1 comprises a retaining element 5 designed to be fitted on the body 2, as shown in the accompanying drawings. The retaining element 5 is designed to be slidably positioned in the duct 3 during the escape of the body 2 from the duct 3, as may be noted in FIGS. 1a and 2a. The retaining element 5 is preferably designed to receive the body 2 in such a way that the body 2 remains inserted through the retaining element 5 during the escape of the body 2 from the duct 3 and the withdrawal of the body 2 in the duct 3.

The retaining element 5 is configured to remain integral with the movement of the body 2 during the escape of the body 2 from the duct 3, and/or to follow the body 2 during the escape of the body 2 from the duct 3.

For this purpose, the retaining element 5 is configured to prevent the sliding of the body 2 relative to the retaining element 5 during the escape of the body 2 from the duct 3.

For this purpose, the device 1 advantageously comprises constraining means between the retaining element 5 and the body 2, configured so that the retaining element 5 is designed to follow and/or to remain integral with the body 2, during the escape of the body 2 from the duct 3.

Advantageously, the constraining means are designed in such a way that the body 2 cannot move with respect to the retaining element 5, except in the situation when the retaining element 5 is gripped to the duct 3, as will be described in more detail below.

The constraining means are therefore designed to prevent the sliding of the body 2 relative to the retaining element 5 during the escape of the body 2 from the duct 3.

Comparing FIG. 1a with FIG. 1b and FIG. 2a with FIG. 2b, it may be noted that, in the first embodiment illustrated, the retaining element 5 does not undergo movements along the body 2, during the escape of the body 2 from the duct 3.

The constraining means preferably form part of the retaining element 5.

The retaining element 5 may be, for example, a self-locking ring suitable to be jammed.

With reference to FIGS. 1b, 1c, 2b and 2c, the retaining element 5 is configured to grip onto the duct 3 in such a way as to allow, during the withdrawal of the body 2 in the duct 3, the sliding of the body 2 relative to the retaining element 5.

The retaining element 5, in the embodiment illustrated, is configured to grip an anchoring section of the duct 3.

The anchoring section corresponds advantageously to the distal section 3a, in the first embodiment illustrated.

The constraining means between the retaining element 5 and the body 2, when the retaining element 5 is gripped to the duct 3, and therefore in the situations of FIGS. 1b, 1c, 2b and 2c, are configured to allow the sliding of the body 2 with respect to the retaining element 5, during the withdrawal of the body 2 into the duct 3.

This sliding preferably occurs along the axis of extension of the duct 3 and/or along the axis of extension of the body 2.

In the embodiment illustrated, starting from the situation of FIG. 1a or 2a, and following the action exerted by the user according to the arrow X, the body 2 escapes from the duct 3, until the retaining ring 5 is locked and/or grips the duct 3, as shown in FIGS. 1b and 2b. In the embodiment illustrated, as mentioned above, the retaining ring 5 is designed to fasten onto the duct 3 on a anchoring section which corresponds to the distal section 3a of the duct 3.

Starting from the situation of FIG. 1b or 2b, wherein the body has surrounded the organ and therefore couples or attaches the distal hook 2a on itself, see FIG. 1c, the user pulls the operating member 4 backwards by applying on the operating member 4a retraction action according to the arrow Y, in such a way as to withdraw the body 2 in the duct 3, and reach, for example, the operating situation shown in FIG. 1c or 2c. In the operating situation of FIG. 1c or 2c, and following the retraction action Y applied by the user, at least a proximal portion 2" of the body 2 enters the duct 3, in such a way that, between the situation of FIG. 1*b* or 2*b* and that of FIG. 1*c* or 2*c*, the extension of the distal portion 2' is reduced.

The reduction of extension cannot be noted in FIGS. 1*b* and 1*c*, at least in detail, since the distal portion 2' is not to scale and it is not coupled on itself in FIG. 1*b*.

In this way, the retaining element 5 is configured to grip onto the duct 3 in such a way that the withdrawal of the body 2 in the duct 3 allows the adjustment of the extension of the distal portion 2' once it has adopted the closed shape.

The withdrawal of the body 2 into the duct 3 allows the inner tension in the distal portion 2' of the body 2 to be adjusted, and/or the system of forces which the distal portion 2' applies on the organ or viscera.

Moreover, thanks to the fact that the constraining means between the body 2 and the retaining element 5 in this way ensure that there is no mutual sliding when the body 2 is escaping from the duct 3, once the user has slid backwards a certain proximal portion 2" of the body 2 relative to the retaining 5 and once the user no longer exerts a retraction action Y, the configuration of the distal portion 2' which derives from this withdrawal remains, at least substantially, unchanged.

In order for the user to easily release the operating member 4 from the body 2, the operating member 4 is designed to release the body 2 after the escape of the operating member 4 from the duct 3, as shown in FIG. 2*d*.

In the first embodiment illustrated the operating member 4 is designed to release the body 2 after the escape of the operating member 4 from the distal section 3*a* of the duct 3.

In order to allow the exerting of the retraction action Y on the operating member 4, after the distal portion 2' has adopted the closed shape and it has been coupled on itself or on the retaining element 5 by the hook 2*a*, and therefore so that the user can cause the withdrawal of the body 2 into the duct 3, the device 1 comprises a block 7 designed to limit the sliding of the operating member 4 inside the duct 3 and/or along the duct 3.

Advantageously, the block 7 is designed to prevent the escape of the operating member 4 from the duct 3. In the embodiment illustrated, the block 7 is designed to prevent the escape of the operating member 4 from the distal section 3*a* of the duct 3.

The block 7 is preferably removable. The block 7 can be associated removably at a proximal end 4*c* of the operating member 4. The proximal end 4*c* of the operating member 4 advantageously comprises a grip with which the user can easily push or withdraw the operating member 4.

Starting from the situation of FIG. 1*a* or 2*a*, the user makes the body 2 escape from the duct 3 by means of the pushing action X, but the block 7 is such that the operating member 4 does not escape from the duct 3, as shown in FIG. 2*b*. After the adjustment of the retaining action of the body 2 on the organ, and, therefore, starting from the situation of FIG. 1*c* or 2*c*, in order to release the device 1 from the body 2 the user removes the block 7, so that the operating member 4 can escape from the duct 3 by a further pushing action X applied by the user, as shown in FIG. 2*d*.

As shown in FIG. 2*d*, when the operating member 4 leaves the duct, the arms 4*a* and 4*b* move away elastically from one another, whilst when the operating member 4 is in the duct 3 the inner surfaces of the duct 3 are configured to force the arms 4*a* and 4*b* to remain mutually closed to stably grip the end of the body 2.

These arms 4*a* and 4*b* may therefore define an elastic joint for the tumbling of the body 2.

The accompanying drawings show a certain distance between the operating member 4 and inner surfaces of the duct 3, or between the lateral surfaces of the retaining element 5 and the inner surfaces of the duct 3.

This distance is functional basically to the clarity of the drawings, and could be much more reduced or zero.

Preferably, the retaining element 5 comprises at least one anchoring spring 8. The anchoring spring 8 is at least partly integral with the retaining element 5, and it may be defined as a non-return spring.

Advantageously, the anchoring spring 8 is configured to adopt an operational sliding condition, wherein it is designed to slide in the duct 3 and/or along the duct 3, during the escape of the body 2 from the duct 3. The operational sliding condition is shown in FIGS. 1*a* and 2*a*.

In the first embodiment illustrated, when the anchoring spring 8 adopts this sliding condition, the retaining element 5 is designed to follow and/or to remain integral with the elongate body 2 during the escape of the elongate body 2 from the duct 3.

Advantageously, the anchoring spring 8 is configured to adopt an operational anchoring condition wherein it is designed to remain anchored and/or blocked to an anchoring section of the duct 3, and/or to oppose the anchoring section. This anchoring condition is shown in FIGS. 1*b*, 1*c*, 2*b* and 2*c*.

Preferably, when the anchoring spring 8 adopts the operational anchoring condition, the anchoring spring 8 is configured so that the retaining element 5 grasps and/or remains gripped to the duct 3, in such a way that, in the direction of withdrawal of the body 2 in the duct 3, the movement of the retaining element 5 relative to the duct 3 is prevented.

According to the embodiment shown, when the anchoring spring 8 adopts the anchoring condition, the constraining means between the retaining element 5 and the body 2 are designed to ensure that the body 2 can slide relative to the retaining element 5, during the withdrawal of the body 2 in the duct 3.

Preferably, the anchoring spring 8 is configured to pass automatically from the sliding condition to the anchoring condition, when the retaining element 5 passes through the anchoring section in the direction of escape of the body 2 from the duct 3.

With reference to FIG. 1*b* or 2*b*, when the retaining element 5 reaches the anchoring section, which in the embodiment illustrated coincides with the distal section 3*a* of the duct 3, the anchoring spring 8 widens, transversely to the axis of extension of the duct 3 and relative to the preceding sliding condition. In this way, the anchoring spring 8 ensures that the retaining element 5 remains locked to the distal section 3*a*, whilst the user exerts the retraction action Y.

In the embodiment illustrated, the spring 8 is designed to remain anchored to the duct 3 pushing on the duct 3 in the direction of withdrawal of the body 2 in the duct 3, and when the user applies the retraction force Y.

In this way, as explained above, the anchoring spring 8 acts in conjunction to ensure that the body 2 can slide relative to the retaining element 5, when the retaining element 5 is gripped to the duct 3 and the user applies a retracting action Y.

Summing up, the user, starting from the situation of FIG. 1*a* or 2*a*, exerts a pushing action X on the operating member 4, whilst the anchoring spring 8 is in the sliding condition and allows the retaining element 5 to follow the body 2 during the escape of the body 2 from the duct 3.

When the retaining element 5 passes through the distal section 3a of the duct 3, the spring 8 passes automatically from the sliding condition of FIGS. 1a and 2a to the anchoring condition of FIGS. 1b and 2b.

When, starting from the situation of FIG. 1b or 2b, the user withdraws the operating member 4 according to the arrow Y to withdraw and re-enter at least a proximal portion 2″ of the body 2 in the duct 3, the anchoring spring 8 keeps the retaining element 5 anchored to the duct 3 and allows sliding of the body 2 relative to the retaining element 5.

Moreover, the retaining element 5 can also be advantageously configured to create a contrast to the coupling or attachment means which make it possible to maintain the at least partly annular shape of the distal portion 2'. In effect, when the user exerts the retraction action in the direction of the arrow Y, if the coupling or attachment means are also withdrawn towards the duct 3 due to the friction with the body 2, the coupling or attachment means rest against the retaining element 5, which advantageously is configured to prevent the coupling or attachment means from following further the withdrawal of the body 2 towards the duct 3 or in the duct 3.

When, starting from the situation of FIG. 2c or 1c, the user again pushes the operating member 4 according to the arrow X, the retaining element 5 remains integral with the body 2, in such a way that the operating member 4 releases the body 2 without varying the inner tension of the distal portion 2', and/or its extension, since the body 2 does not slides relative to the retaining element 5. In other words, the distal portion 2' thereby maintains the configuration adopted previously, since the constraining means between the body 2 and the retaining element 5 ensure that, when the body 2 moves to escape from and/or away from the duct 3, the retaining element 5 remains integral with the body 2.

It should however be noted that, preferably, the constraining means between the body 2 and the retaining element 5 ensure that the body 2 always remains securely integral and it does not move relative to the retaining element 5, except in the situation wherein the retaining element 5 is anchored to the duct 3 and the body 2 is subject to a retraction action Y at least to a certain extent, which can overcome the force which the constraining means oppose to the sliding of the body 2 relative to the retaining element 5, the latter sliding being understood to be in the direction of withdrawal of the body 2 into the duct 3.

A possible method of operation or of use of a device 1 according to this invention, or to operate the device 1, comprises exerting a pushing action X on the operating member 4 in order to cause the escape of the elongate body 2 from the duct 3, so that at least one distal portion 2' of the elongate body 2 adopts a closed shape and/or at least partially annular, and so that the retaining element 5 grips the duct 3.

This method then comprises the coupling or attaching of the distal portion 2' to itself or to the retaining element 5 in such a way that it maintains this shape.

This method then comprises exerting a retraction action Y opposite to the thrust action X to cause the withdrawal of the elongate body 2 into the duct 3, in such a way as to adjust the extension and/or the inner tension of the distal portion 2' once it has adopted this shape.

The method preferably comprises a further step comprising applying a further pushing action X on the operating member 4 so that it escapes from the duct 3 in such a way that the retaining element is released with the elongate body 2. This method, prior to the further step and in order to perform this further step, preferably comprises the step of removing a block 7 designed to limit the sliding of the operating member 4 along the duct 3 and/or in the duct 3.

FIG. 3 shows the surgical device with all the elements described in which the duct 3 is equipped with a relative grip 3b. The operating member comprises the operating rod 4, with the handgrip 4c the joint for tumbling the distal end 2b of the body 2 and the removable block 7 limiting the travel of the rod 4. The body 2 has the proximal end 2b reversibly joined to the rod 4 of the operating member thanks to coupling means 4a and 4b for the tumbling of the end 2b of the body when it escapes from the duct 3. The operating member comprises the block 7, removable by the surgeon, which limits the sliding of the operating member 4 inside the duct 3. The limitation prevents the escape and therefore the involuntary freeing of the retaining element 5.

At the distal end of the body 2 there are coupling or attachment means 2a, with which it anchors the stretch 2' of the body on itself or with the retaining element 5. The stretch 2' of the body has along its circumferential path gripping means P designed for an atraumatic gripping of the laparoscopic instruments and grippers.

The spring M, in this non-limiting drawing, extends from the distal end of the body, where there is the attachment or coupling element 2a, and continues upstream of the proximal end of the body integral with the rod, as shown in the drawing, or integral directly with the grip Mb which is useful for extracting the spring M.

The predetermined curvature of the spring M facilitates the body in the wrapping around of the organ. The same spring moves the coupling or attachment means 2a closer to the retaining element 5 or to the stretch 2' of the body.

The retaining element 5 has an anchoring element 8 at the distal end section of the duct 3a and constraining means 8a such as, for example, a self-locking ring suitable to be jammed.

The operating member has a control grip 4c which acts on the rod 4 as pushing or withdrawal means.

Table II FIG. 4 shows another possible configuration, not to scale, of the retaining element 5 in which can be seen the anchoring means 8 and the constraining means 8a which can be easily de-activated by the surgeon to pass from a step of preventing the sliding to another moment of free sliding of the body in the retaining element also in a step wherein the retaining element is no longer clinging to the duct. By way of example, FIG. 4 shows the constraining element as a choker button system which locks the body and only when flattened by the surgeon allows the free sliding of the body through the retaining element.

Further, FIG. 4 shows a recess in the retaining element aimed at receiving the coupling means 2a.

FIG. 5 shows, by way of example and without limiting the scope of the invention, the complete surgical device as it is released around the organ at the end of the application. In order to better show certain details of the surgical device the opening of the coupling or attachment means 2a remains. The gripping means P for laparoscopic instruments is shown, the body 2 inserted in the retaining element 5. The latter shows the anchoring ring 8 and the constraining means 8b represented by a spring button.

The body 2 with the proximal end 2b and the proximal portion 2″ withdrawn and recessed relative to the retaining element; the distal portion 2' which surrounds the organ and the distal end with the coupling or attachment means in this case, by way of example, represented by a first spherical magnet with a connecting and coupling pin positioned at the distal end of the body 2a. The second magnet which attracts the first is housed in the bottom of a recess N, made in the retaining element 5. In continuity with the recess there is a slot in which lies with a bayonet system the pin of the first magnet which opposes any opening of the surgical device.

In the retaining element 5 is formed a guide recess N to the access in the bottom of which is housed the second magnet but offset relative to the access in such a way not only to attract the first in the bottom but also to translate towards a slot in continuity with the recess in which lies with a bayonet system the pin of the first magnet which opposes any opening of the surgical device; so that it is sufficient to bring the attachment means to the guide area to the access to obtain the automatic attraction of the coupling means in an irreversibly locked position.

FIGS. 6 and 7 show a very simplified second embodiment of the invention wherein the elongate body 2 comprises a partly circumferential inflatable structure 9, the ends of which are labelled 9a and 9b.

The device according to this second preferred embodiment is connected to the inflation means such as, for example, a simple syringe. The connection is made through the pipe 10b which extends from a valve 10b', preferably unidirectional, to the opposite end 10b" which reaches the inflation means through the operating member, not illustrated.

For this purpose, the pipe 10b is in fluid-dynamic communication at a first end, the valve 10b', with the inside of the inflatable structure 9, and, at a second end 10b" opposite the first end 10b', with the pumping means.

The valve is therefore preferably in fluid-dynamic communication with the pumping means by means of the pipe 10b.

The valve 10b' may advantageously be positioned near the proximal end of the body 9, closest to the operating member. After the desired inflation, the pipe 10b may advantageously be removable from the valve 10b' and, therefore, detached from the body 9.

The inflatable structure 9 is shown in FIG. 6 in the deflated configuration.

FIG. 7 shows the same structure 9 in the inflated configuration, where the two opposite ends 9a and 9b automatically in contact can be seen.

In the inflated configuration, the structure 9 is preferably more rigid than when in the deflated configuration, but it is in any case elastic so that it can be positioned correctly without damaging the organ. The inner wall of the body, the one in contact with the tissues, has a non-slip surface which prevents the shifting or the slipping of the surgical device from the seat in which has been positioned.

With this second embodiment, the surgeon uses the operating member, not shown in FIGS. 6 and 7, to push the inflatable structure 9 outside the duct and inflate under pressure the surgical device, therefore rendering the coupling means 9a and 9b integral and closing completely the circumference around the organ, so that it can perform, like the distal portion 2' of the first embodiment, the circumferential constraining function.

In the embodiments described, the elongate body 2 of FIGS. 1, 2, 3 and 5 and the body 9 of FIGS. 6 and 7, is made preferably at least partly of a radio opaque and, therefore, which can be detected by X-rays.

The invention provides a compact suspensor device which is able to provide a constraining system for at least one organ in a fast and easy manner, without having to apply excessive forces on the organ, in such a way as to prevent the occurrence of traumas on the same organ or viscera.

Moreover, the device allows the user to have a correct perception in the performance of the various steps which make up the preparation of the constraining system, in such a way as to reduce the risk that incorrect forces are exerted which might adversely affect a correct preparation of the constraining system.

With the device according to this invention, the surgical device becomes practically the interface between the surgeon and the anatomical structures. A firm instrumentation grip exclusively on the surgical device forms a true "not touch technique" in full respect of the tissues. The surgical manoeuvres are facilitated, the intervention time is reduced, the tears and the bleeding which occurs with the direct gripping on organs or viscera is avoided.

The invention claimed is:

1. A device for laparoscopic surgical operations, comprising two distinct structures assembled together, formed by an elongated, ribbon-like, soft, but durable body (2), and by a retaining element (5) suitable to be slidably fitted on said body, being said device configured to be used to move an organ or viscera and is applicable through a duct (3) in which a control member slides (4), and which can be removed together with the control member after that the device is positioned, being said device designed to not require the use of a dedicated trocar access to the abdominal pockets for the introduction of an external handpiece; wherein said body is arranged to accommodate in its interior a removable spring (M) along its length and, for this purpose, the spring can be either adapted to the rod (Ma), or to the handle (Mb), which is helpful for the extraction of said spring (M) that should be filiform, accessing from the proximal end of said body and continuing to the distal end without puncturing it and tending to resiliently assume a form at least partially annular, for transmitting said shape to at least a distal portion (2') of said body, being said spring (M) useful to surround the organ or the bowels and to bring the distal end of said body (2a) to the distal portion (2') of the same element or the retaining body (5).

2. A device according to claim 1, wherein said elongated body has, at the distal end a means of attachment or coupling (2a), configured so that at least a distal portion of said body engages or attacks on itself or on the retaining element, thereby allowing it to complete the irreversible circumferential closure of the device enveloping organs or bowels.

3. A device according to claim 2, wherein the means of coupling or attaching are magnetic, with a first magnet positioned on the distal end of the body 2a and a second magnet allocated at the bottom of an adapted slot (N) that is positioned on the retaining element, so that the latter magnet attracts the coupling means getting close to that area and automatically draws it in an irreversible anchoring or locking manner.

4. A device according to claim 1, wherein said body has gripping means (P) implanted along its outer surface for the whole circumference so that these gripping means can be gripped by specially crafted tools and laparoscopic forceps once the means of attachment or coupling are locked or tightened, thereby allowing the operator to move or abandon said organ or viscera depending on the needs related to the surgical procedure, without directly touching it or directly touching the device.

5. A device according to claim 1, wherein the proximal portion (2") of the body presents a coupling element (2b) at the proximal end with which said body is connected to the tool of maneuver and follows the advances or retractions exerted by said maneuvering tool.

6. A device according to claim 1 wherein the proximal portion (2") of the body presents a coupling element (2b) at the proximal end with which said body is connected to the tool of maneuver and follows the advances or retractions exerted by said maneuvering tool, and wherein said operating member (4) presents said coupling means (4a and 4b) that are configured so that they are adapted to automatically release said proximal end of the body with the coupling element, as a result of the output of said operating member from said conduit.

7. A device according to claim 1, comprising a block (7) suitable to limit the sliding of said operating member inside and/or along said duct, thereby preventing the output of said operating member from said conduct, being said block removable.

8. A device according to claim 1 wherein said elongated body has, at the distal end a means of attachment or coupling (2a), configured so that at least a distal portion of said body engages or attacks on itself or on the retaining element, thereby allowing it to complete the irreversible circumferential closure of the device enveloping organs or bowels, and wherein said retaining element, which is adapted for being arranged inside said duct, is suitable to receive said body so that said body slides and remains inserted through said retaining element.

9. A device according to claim 1 wherein said retaining element comprises at least one anchoring spring (8), in which the anchoring spring is configured to assume a sliding operating condition, in which it is suitable for sliding in said conduit and/or along said conduit, during the discharge of said stretched body from said conduit, so that, when the anchoring spring assumes that sliding condition, the retaining element is suitable to follow and/or remain joined to the elongated body during the discharge of said elongated body from said conduit, wherein said fixing spring is configured to assume an operative condition in which the anchor is suitable to remain anchored and/or locked to an anchoring section of the distal end of said conduit, and/or contrasting with said anchoring section, so that, when such anchoring spring assumes the operating anchoring condition, the same anchoring spring allows the said retaining element to cling and/or to remain clung to said conduct, so that the movement of said retaining element in said conduit in the same direction of recession of said body in said conduit is prevented so that said retraction allows to adjust the extension and/or the internal voltage of said distal portion (2'), with the closing of means of attachment or coupling, has assumed said form at least partially annular and wherein said fixing spring is configured to automatically switch from said sliding condition to said anchoring condition, when said retaining element passes through the said anchor section in the direction of the discharge of said body from said conduit.

10. A device according to claim 1, wherein said retaining element, comprising connecting means between said body and said retaining element are adapted for preventing the sliding of said body relative to said retaining element which are rigidly coupled, during said discharge of said body from said duct, and once said coupling element is clung to the distal end of said conduit, being suitable to allow the sliding of said body relative to said retaining element during said retraction of said body in said conduit, being this constraining means for example a self-locking ring suitable to be jammed.

11. A device according to claim 10, wherein said constraint means have the possibility to be temporarily inactivated by the surgeon, by acting by means of laparoscopic forceps on one (8a) tightening dispositive located on the retaining element.

12. A device according to claim 1, in which the removable maneuver tool is coupled to a thrust and retraction member through which the discharge or the retraction of the body from the conduit 3 is determined.

13. A device according to claim 1 limited to only one element, the partially annular body, comprising a simple pneumatic structure (9), inflatable, connected to means for inflating the transmission to the proper pressure to obtain a predetermined shape and volume, but which when deflated has an elongated, ribbon-like shape, low in volume and free of texture, but resistant, which facilitates its introduction with the laparoscopic instruments in use, without the use of any other dedicated tool, maneuvering member or trocar access to the abdominal cavity.

14. A device according to claim 1 limited to only one element, the partially annular body, comprising a simple pneumatic structure (9), inflatable, connected to means for inflating the transmission to the proper pressure to obtain a predetermined shape and volume, but which when deflated has an elongated, ribbon-like shape, low in volume and free of texture, but resistant, which facilitates its introduction with the laparoscopic instruments in use, without the use of any other dedicated tool, maneuvering member or trocar access to the abdominal cavity, in which said means of transmission include a one-way inflation valve positioned on said body and a pipe (10b) which is in fluid communication, on a first end (10b'), with said valve communicating with said body and, on a second end (10b") which is opposite to said first end, with the pumping means.

15. A device according to claim 1, wherein said pneumatic body of predetermined shape and volume uses said inflation pressure in order to regain said body to said partially annular shape which facilitates its application on the bowels or organ during laparoscopy, it activates the mechanism of coupling of the two ends, proximal and distal, of said body to which said means of coupling or attack are connected, and finally it exposes on its surface said attachment means (P) for laparoscopic tools and pliers.

* * * * *